April 25, 1961 E. HARRIS Plant Pat. 2,051
PECAN TREE
Filed April 4, 1960
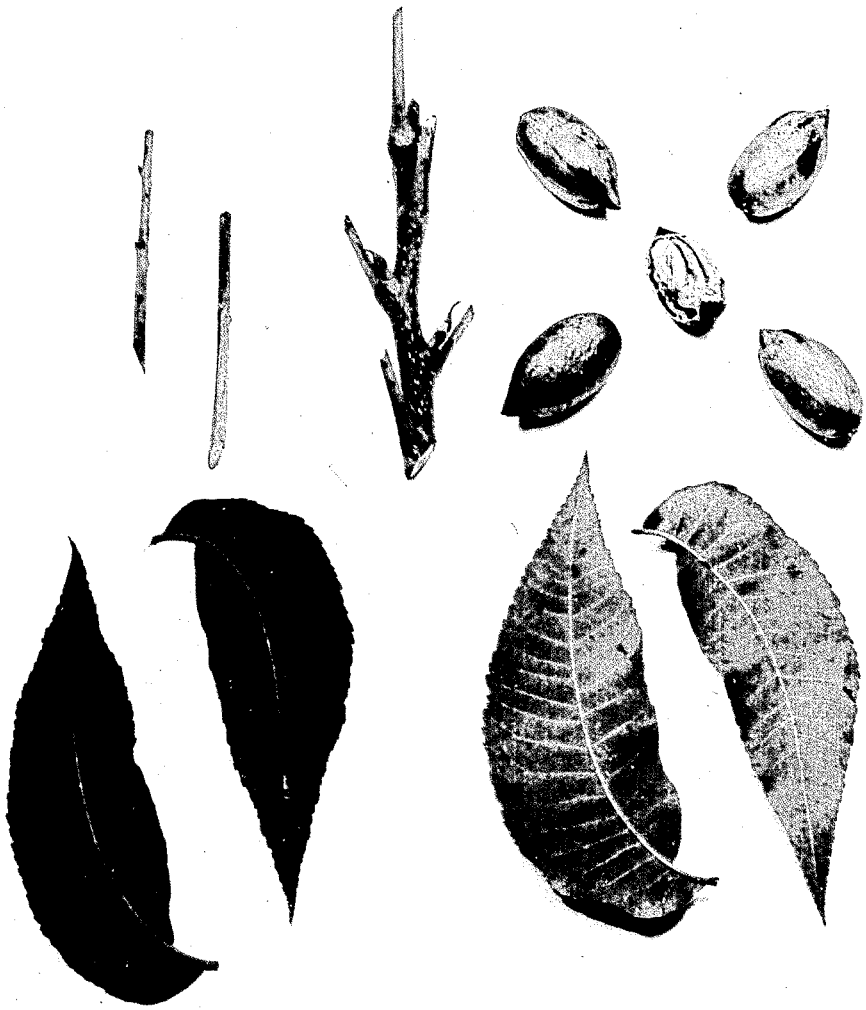
INVENTOR
Edward Harris
BY Robb & Robb
ATTORNEYS United States Patent Office Plant Pat. 2,051
Patented Apr. 25, 1961

2,051

PECAN TREE

Edward Harris, Gunnison, Miss., assignor to Simpson Nursery Company, Monticello, Fla., a partnership Filed Apr. 4, 1960, Ser. No. 19,973

1 Claim. (Cl. 47—62)

The present invention relates to a new and distinct variety of pecan tree, which was discovered by me as a newly found seedling on my cultivated farm property at Gunnison, Mississippi.

My attention was first attracted to this new seedling when it grew up beside a pecan tree of the variety known as "Stuart" (unpatented) then growing in my orchard. When this new seedling bore its first nuts, I found that the nuts were superior to those of the "Stuart" variety and many others, and I cut down the adjacent "Stuart" tree so as to afford more growing room for the new seedling. The new seedling was then carefully preserved and kept under close observation. In due course, asexual reproductions were made thereof, as performed by me by budding at Gunnison, Mississippi, and as made on my behalf by grafting, as performed by my assignee at Monticello, Florida, and came true to form, corresponding in all respects to the original seedling. Observations of the asexual reproductions fully confirmed the distinctions and superiority of the tree and nuts of the original seedling, and convinced me that it is a new and distinct variety.

Although the parentage of the new seedling is not definitely known to me, I believe it resulted from an open-pollinated cross between the "Stuart" variety and the variety known as "Schley" (unpatented). The nuts of the new seedling resemble those of "Schley" in some respects, but the kernels of the nuts of the latter are smoother and a little more oily. Of great commercial importance is the fact that my new variety is much more resistant to pecan scab.

By way of a brief résumé of the superior features of my new pecan seedling, the following outstanding characteristics have been noted and are considered as representing a unique combination which differentiates said new seedling from all other pecan varieties of which I am aware:

(1) A heavy bearing habit;

(2) Large size and distinctive form of the nuts which have longer points than any other important commercial pecan variety of which I am aware;

(3) Very thin nut shells which are much thinner than those of the "Stuart" variety, resulting in easier separation of the shell and partitions from the kernels;

(4) Plump, well-filled kernels comparable to "Schley," but not as smooth;

(5) An attractive, light amber color of the kernels and an abundance of oil therein, but not as oily as the kernels of "Schley" nuts; and (6) Good resistance to pecan scab, as evidenced by the fact that my new variety has consistently borne heavy nut crops when the crops of "Stuart," "Schley" and other varieties were lost as the result of pecan scab.

The accompanying drawing shows typical specimens of the foliage, leaf rachis, wood and nuts of my new variety, with both the upper and under surfaces of specimen leaflets being depicted, and with one of the individual nut specimens having its shell partially broken away to expose the kernel, all as depicted in color as nearly true as it is reasonably possible to make the same in a color illustration of this character.

The following is a detailed description of my new pecan variety, with color terminology in accordance with Koster's Color Guide, except where general color terms of ordinary dictionary significance are obvious, as based upon observations made at both Gunnison, Mississippi, and Monticello, Florida:

Tree: Large size; good productivity; regular bearer; vigorous growth; medium stocky limbs. Wood—smooth; color: old wood—near Maroon, Plate 97; young wood: upper surface—near Lavender Blue, Plate 64; under surface—near Lettuce Green, Plate 74.

Foliage:

*Size.*—Large; mature leaves measure up to about 16 inches to 20 inches long; leaflets measure up to about 3 inches to 7 inches long and 1 inch to 1¾ inches wide.

*Quantity.*—Heavy; average 13 to 15 leaflets per leaf.

*Color.*—Upper side—near Taxus Green, Plate 81. Under side—near Boxwood Green, Plate 79.

Buds:

*Shape.*—Three buds to each leaf, with buds close together and top bud being large and pointed. In the view shown, only one bud appears at each leaf node.

*Color.*—Brown.

Nuts:

*Ripening habit.*—Even.

*Dates of first and last picking.*—About November 1 and about December 1, respectively; average time of harvesting is about mid-season.

*Quantity.*—Heavy bearing.

*Tenacity.*—Releases from shucks very easily.

*Cluster.*—Medium size; from 3 to 5 nuts per cluster, with average 4 nuts per cluster.

*Individual nuts.*—Size—large. Length—about 1⅞ inches. Diameter—about 1 inch. Average number of nuts to pound—about 45. Shape—long; blunt at one end; long point at opposite end. Shell—Thin (about 1/32 inch); cracks and releases very easily; color—near Bistre, Plate 93, but somewhat redder in range toward Mahogany, Plate 95. Kernel: color—near Buff, Plate 90; flavor—rich; shape—long; texture—fine; sutures—even.

Disease resistance: Very good resistance to pecan scab, as evidenced by comparison with other varieties grown under comparable cultural conditions in same localities at Gunnison, Mississippi, and Monticello, Florida.

Keeping quality: Very good.

I claim:

A new and distinct variety of pecan tree, substantially as herein shown and described, characterized particularly as to novelty by the unique combination of a heavy bearing habit, large size and distinctive form of the nuts which have a long point on one end, very thin nut shells resulting in easy separability of the shell and partitions from the nut kernels, plump, well-filled kernels comparable to those of the variety "Schley" (unpatented), but not as smooth as the latter, the abundance of oil in the nut kernels, but not as oily as those of "Schley," an attractive light amber color of the kernels, and very good resistance to pecan scab.

No references cited.